(12) United States Patent
Zhang (10) Patent No.: US 10,918,823 B2
(45) Date of Patent: Feb. 16, 2021

(54) DISPLAY CONTROL METHOD AND DEVICE (71) Applicant: BOE TECHNOLOGY GROUP CO., LTD., Beijing (CN)

(72) Inventor: Xiao Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 279 days.

(21) Appl. No.: 15/861,217

(22) Filed: Jan. 3, 2018

(65) Prior Publication Data
US 2018/0185609 A1    Jul. 5, 2018

(30) Foreign Application Priority Data
Jan. 3, 2017    (CN) .......................... 2017 1 0003880

(51) Int. Cl.
| A61M 21/02 | (2006.01) |
| G06F 16/735 | (2019.01) |
| G06K 9/00 | (2006.01) |
| G06F 16/783 | (2019.01) |
| A61B 5/00 | (2006.01) |
| A61B 5/1171 | (2016.01) |

(Continued)

(52) U.S. Cl.
CPC ............ *A61M 21/02* (2013.01); *A61B 5/1176* (2013.01); *A61B 5/4809* (2013.01); *A61B 5/4812* (2013.01); *A61B 5/4836* (2013.01); *G06F 16/735* (2019.01); *G06F 16/7837* (2019.01); *G06K 9/00275* (2013.01); *A61B 5/165* (2013.01); *A61B 2503/06* (2013.01); *A61M 2021/005* (2013.01); *A61M 2021/0027* (2013.01); *A61M 2205/3592* (2013.01); *A61M 2205/505* (2013.01); *A61M 2205/6009* (2013.01); *A61M 2230/63* (2013.01); *G06K 2009/00322* (2013.01)

(58) Field of Classification Search
CPC ............. A61M 21/00–02; A61B 5/4809–4812
See application file for complete search history.

(56) References Cited

U.S. PATENT DOCUMENTS

| 2015/0326900 | A1 | 11/2015 | Yoshizawa |
| 2017/0182283 | A1* | 6/2017 | Palmateer ............. A61M 21/02 |

FOREIGN PATENT DOCUMENTS

| CN | 102263999 A | 11/2011 |
| CN | 103531216 A | 1/2014 |

(Continued)

OTHER PUBLICATIONS

First Office Action for Chinese Application No. 201710003880.1, dated Dec. 28, 2018, 12 Pages.

(Continued)

*Primary Examiner* — Thaddeus B Cox
(74) *Attorney, Agent, or Firm* — Brooks Kushman P.C.

(57) ABSTRACT

A display control device and a display control method are provided. The display control method includes: acquiring current data of a user, the current data including identity information of the user and current time; matching the current data with feature parameters of video contents in a video database; and in case that the current data is matched with the feature parameters of the video contents successfully, setting the video contents as contents to be played, wherein the video contents include audio information and video information.

15 Claims, 3 Drawing Sheets

(51) Int. Cl.
   *A61M 21/00*     (2006.01)
   *A61B 5/16*      (2006.01)

(56) References Cited

FOREIGN PATENT DOCUMENTS

| | | |
|---|---|---|
| CN | 104699248 A | 6/2015 |
| CN | 104853229 A | 8/2015 |
| CN | 104871548 A | 8/2015 |
| CN | 105338405 A | 2/2016 |
| CN | 105933539 A | 9/2016 |

OTHER PUBLICATIONS

1st Chinese Office Action, English Translation.
CN102263999A, English Abstract and Machine Translation.
CN103531216A, English Abstract and Machine Translation.
CN104699248A, English Abstract and Machine Translation.
CN104853229A, English Abstract and Machine Translation.
CN104871548A, English Abstract and U.S. Equivalent U.S. Pub. No. 2015/0326900.
CN105338405A, English Abstract and Machine Translation.
CN105933539A, English Abstract and Machine Translation.

\* cited by examiner

DISPLAY CONTROL METHOD AND DEVICE

CROSS-REFERENCE TO RELATED APPLICATION

This application claims priority to Chinese Patent Application No. 201710003880.1 filed Jan. 3, 2017, which is incorporated herein by reference in its entirety.

TECHNICAL FIELD

The present disclosure relates to a field of display techniques, and in particular, relates to a display control method and a display control device.

BACKGROUND

Sleep quality is closely related to heath of a human body. For a child, staying up late or sleep deprivation may cause reduced growth hormone secreted by the pituitary gland of the child, which in turn may affect a height of the child adversely. Furthermore, if the child's sleep is deprived, the child may feel tired, become fidgety and cranky, or even fall into a hyper mood which makes the child unable to sleep. The hyper mood may cause the child's blood pressure to increase, and make the child's breath and heart rate to be accelerated. If the hyper mood lasts for a long time, the child's development may be adversely affected.

An adult usually lulls his or her child to sleep by using toys or singing songs so as to help the child to fall asleep faster. However, because types of the toys or the songs provided by the adult are usually limited, the child may lose interest in them, and thus an effect of the lulling may be lowered. Additionally, the lulling by the adult is time-consuming and strenuous and may not help the child to develop a habit of falling asleep on his or her own.

SUMMARY

Embodiments of the present disclosure provide a display control device and a display control method, the display control device and display control method include the following technical solutions.

In a first aspect, the present disclosure provides a display control method which includes: acquiring current data of a user, the current data including identity information of the user and current time; matching the current data with feature parameters of video contents in a video database; and in case that the current data is matched with the feature parameters of the video contents successfully, setting the video contents as contents to be played, wherein the video contents include audio information and video information.

Optionally, after acquiring the current data of the user and before matching the current data with the feature parameters of the video contents in the video database, the method further includes: matching the identity information of the user with preset identity information; and in case that the identity information of the user is matched with the preset identity information successfully, matching the current data with the feature parameters of the video contents in the video database.

Optionally, the display control method further includes: playing the contents to be played; acquiring expression features of the user, and generating video preference data according to the expression features; and adjusting the video contents in the video database according to the video preference data.

Optionally, after acquiring the current data of the user, the method further includes: generating a lulling instruction; acquiring behavior feature data of the user according to the lulling instruction, and determining a stage of a sleep process that the user is in according to the behavior feature data; and acquiring a control instruction matched with the stage of the sleep process that the user is in, and executing corresponding operations on the contents to be played according to the control instruction.

Optionally, the generating a lulling instruction includes: acquiring the current time, and matching the current time with preset sleep time; and in case that the current time is matched with the preset sleep time successfully, generating the lulling instruction.

Optionally, in case that the stage of the sleep process that the user is in is determined to be a waking stage, the acquiring the control instruction matched with the stage of the sleep process that the user is in and executing the corresponding operations on the contents to be played according to the control instruction, includes: acquiring a first control sub-instruction matched with the waking stage; selecting first video sub-contents matched with the waking stage from the contents to be played according to the first control sub-instruction; and playing audio information and video information in the first video sub-contents.

Optionally, in case that the stage of the sleep process that the user is in is determined to be a first sleepy stage, the acquiring the control instruction matched with the stage of the sleep process that the user is in and executing the corresponding operations on the contents to be played according to the control instruction, includes: acquiring a second control sub-instruction matched with the first sleepy stage; selecting second video sub-contents matched with the first sleepy stage from the contents to be played according to the second control sub-instruction; and playing audio information and video information in the second video sub-contents.

Optionally, in case that the stage of the sleep process that the user is in is determined to be a second sleepy stage, the acquiring the control instruction matched with the stage of the sleep process that the user is in and executing the corresponding operation on the contents to be played according to the control instruction, includes: acquiring a third control sub-instruction matched with the second sleepy stage; shutting down display of video information in the contents to be played according to the third control sub-instruction, and outputting audio information in the contents to be played; wherein the second sleepy stage is closer to a pre-sleep stage than the first sleepy stage.

Optionally, in case that the stage of the sleep process that the user is in is determined to be a pre-sleep stage, the acquiring the control instruction matched with the stage of the sleep process that the user is in and executing the corresponding operations on the contents to be played according to the control instruction, includes: acquiring a fourth control sub-instruction matched with the pre-sleep stage, shutting down display of video information in the contents to be played according to the fourth control sub-instruction, and reducing an outputted volume of audio information in the contents to be played.

Optionally, in case that the stage of the sleep process that the user is in is determined to be a shallow sleep stage, the acquiring the control instruction matched with the stage of the sleep process that the user is in and executing the corresponding operations on the contents to be played according to the control instruction, includes: acquiring a fifth control sub-instruction matched with the shallow sleep stage; shutting down display of video information in the contents to be played according to the fifth control sub-instruction, and turning off output of audio information in the contents to be played.

Optionally, in case that the stage of the sleep process that the user is in is determined to be a deep sleep stage, the method further includes: receiving a shutdown instruction, and executing a shutdown operation.

Optionally, the display control method further includes: recording a time length of the sleep process; and adjusting the preset sleep time according to the recorded time length.

In a second aspect, the present disclosure provides a display control device which includes: a processor; a data collector connected with the processor and configured to acquire current data of a user and output the current data to the processor, the current data including identity information of the user and current time; and a storage connected with the processor and configured to store a video database, wherein the processor is configured to: acquire the current data of the user from the data collector, match the current data with feature parameters of video contents in the video database, and in case that the current data is matched with the feature parameters of the video contents successfully, set the video contents as contents to be played, wherein the video contents include audio information and video information.

Optionally, the display control device further includes: a display, connected with the processor and configured to play the contents to be played; and a wireless transceiver connected with the processor, wherein the data collector is connected with the processor through the wireless transceiver, and the wireless transceiver is configured to transmit output signals of the data collector to the processor wirelessly.

Optionally, after the processor acquires the current data of the user and before the processor matches the current data with the feature parameters of the video contents in the video database, the processor is further configured to: match the identity information of the user with preset identity information; and in case that the identity information of the user is matched with the preset identity information successfully, match the current data with the feature parameters of the video contents in the video database.

Optionally, the processor is further configured to: play the contents to be played; acquire expression features of the user, and generate video preference data according to the expression features; and adjust the video contents in the video database according to the video preference data.

Optionally, after the processor acquires the current data of the user from the data collector, the processor is further configured to: generate a lulling instruction; acquire behavior feature data of the user according to the lulling instruction, and determine a stage of a sleep process that the user is in according to the behavior feature data; and acquire a control instruction matched with the stage of the sleep process that the user is in, and execute corresponding operations on the contents to be played according to the control instruction.

Optionally, in case that the processor is configured to generate the lulling instruction, the processor is further configured to: acquire the current time, and match the current time with preset sleep time; and in case that the current time is matched with the preset sleep time successfully, generate the lulling instruction.

In a third aspect, the present disclosure provides a non-transient storage medium which includes instructions and a video database stored on the non-transient storage medium, wherein, when the instructions are executed by a processor, the processor executes the above method.

BRIEF DESCRIPTION OF THE DRAWINGS

In order to illustrate technical solutions of embodiments of the present disclosure more clearly, accompanying drawings used in description of the embodiments are briefly introduced below. Obviously, the accompanying drawings introduced below are only some of the embodiments of the present disclosure. Those of ordinary skills in the art may also derive other drawings from these accompanying drawings without paying creative efforts.

REFERENCE NUMERALS

10—video database; 20—data collector; 30—controller; 40—player; 50—wireless transceiver; 200—data collector; 300—processor; 400—storage; 500—display; 600—wireless transceiver; 700—bus.

DETAILED DESCRIPTION

The technical solutions of the embodiments of the present disclosure will be described clearly and completely in combination with the accompanying drawings of the embodiments of the present disclosure. Obviously, the described embodiments are only some, but not all, of the embodiments of the present disclosure. All of other embodiments obtained by those of ordinary skills in the art without paying creative work fall into the scope of the present disclosure.

Figure 1:
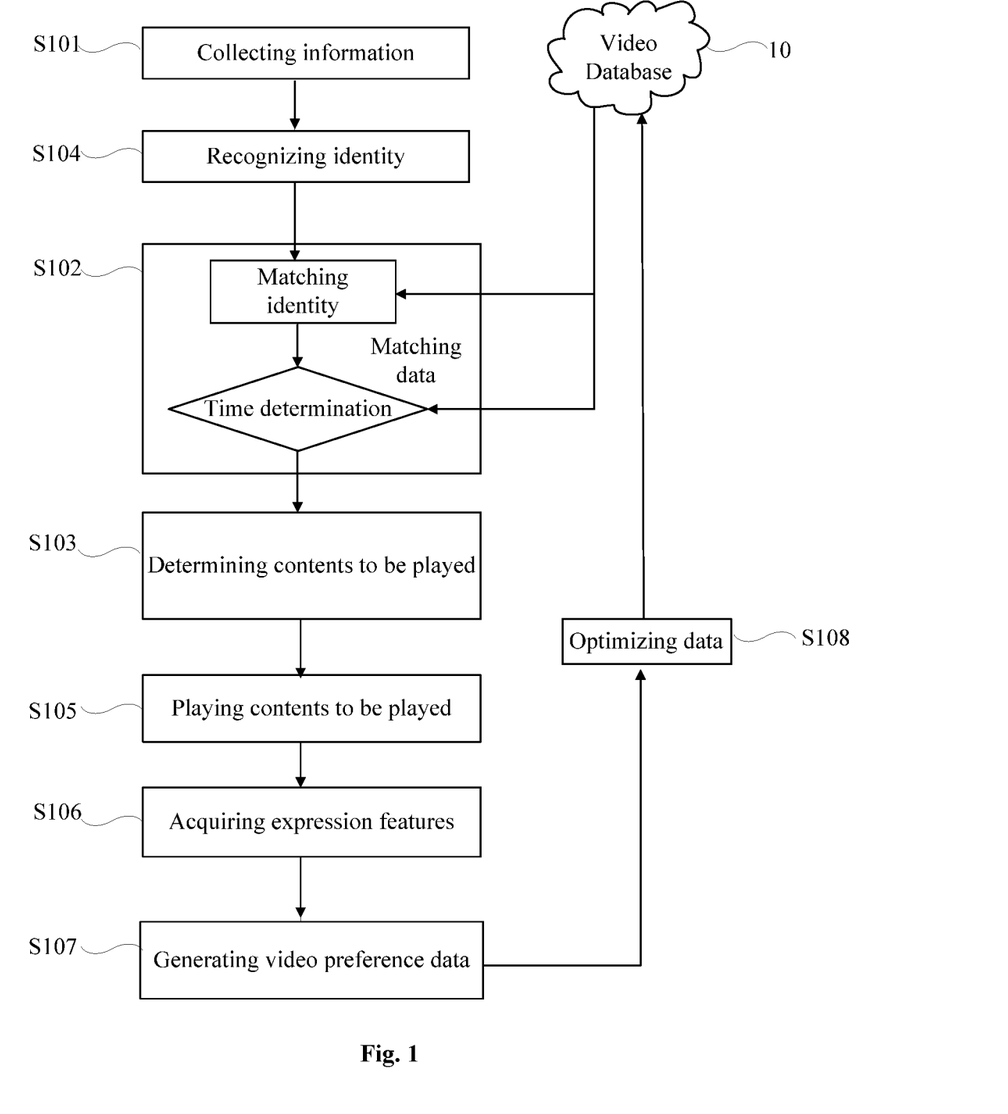
FIG. 1 is a flowchart of a display control method provided by the embodiments of the present disclosure.

As shown in FIG. 1, the embodiments of the present disclosure provide a display control method, and the display control method includes steps S101 to S108.

S101: collecting information.

Specifically, the step S101 may include acquiring current data of a user. The current data includes identity information of the user and current time. The identity information of the user may be an age of the user. It should be noted that the age of the user is not limited in the present disclosure. For example, the age of the user may be 0 to 3, 3 to 6, and the like.

Facial and physical features of the user may be collected by a camera, and the age of the user may be estimated based on the facial and physical features. The age of the user may be inputted by voice and remote control buttons manually. A way in which the identify information of the user is acquired is not limited in the present disclosure.

S102: matching data.

Specifically, the step S102 may include matching the current data of the user acquired in the step S101 with feature parameters of video contents in an video database 10, wherein matching the current data of the user with the feature parameters of video contents in the video database may include matching the identity information of the user with the feature parameters of video contents in the video database, i.e. matching identity, and matching the current time with the feature parameters of video contents in the video database, i.e. time determination. The video contents may include audio information and video information.

A plurality of video contents may be stored in the video database 10. The feature parameters of video contents may include a category to which video information in the video contents belongs. For example, the video information belongs to an animation category, a song & dance category, a drama category, a comedy category, or the like. Based on this, the feature parameters of video contents may be specific contents of the video information in the video contents. For example, in case that the category to which the video information belongs is the animation category, the specific contents of the video information may be also divided according to different animation characters.

The feature parameters of video contents may be a category to which audio information in the video contents belongs. For example, the audio information may belong to a ballad category, a classical music category, a pop music category, a nursery rhyme category, or the like. Based on this, the feature parameters of the video contents may be specific contents of audio information in the video contents. For example, in case that the category to which the audio information belongs is the nursery rhyme category, the specific contents of audio information may also be divided according to different singers. Moreover, the feature parameters of video contents may be a softness of voice in the video contents.

Moreover, the video contents may be stored in a device (referred to as display control device hereinafter) which may implement the display control method provided by the present disclosure. Specifically, the video contents may be set according to common preferences of users of different ages by a manufacturer that produces the display control device, or may be inputted by a user that purchases the display control device. The video contents may be updated by a user according to preferences of the user or a ward (such as a child).

S103: determining contents to be played.

Specifically, in case that the current time in the current data and the identity information of the user are matched with the feature parameters of video contents successfully, the video contents may be used as contents to be played For example, in case that the age of the user in the current data acquired in the step S101 is in the range of 0 to 3, video contents with feature parameters matched with the age may include video information belonging to the animation category or audio information belonging to the nursery rhyme category. In such a case, video contents with video information belonging to the animation category or the nursery-rhyme category may be used as the contents to be played.

In case that the current time in the current data is night, video contents with feature parameters matched with night may include soft animations or voices. In such a case, video contents with the soft animations or voices may be used as the contents to be played, i.e. first contents to be played.

In case that the current time in the current data is morning, video contents with feature parameters matched with morning may include clear and melodious animations or voices. In such a case, video contents with the clear and melodious animations or voices may be used as the contents to be played, i.e. second contents to be played.

In view of the above, the current data may be collected by the display control method. On one hand, because the current data includes the identity information of the user, video contents to be played may correspond to the identity information of the user when the feature parameters of video contents to be played are matched successfully with the identity information of the user. In such a way, a match degree between the contents to be played and interest and attention of the user may be increased, so that the user, such as a child, may be in a state of devoting himself into watching and listening when the contents to be played are played. On the other hand, because the current data may also include the current time, video contents to be played with feature parameters matched with the current time may be used to lull a child to sleep when the current time is night. In such a way, a child who devotes himself or herself to the video contents sufficiently may be hypnotized efficiently and an effect of lulling the child to sleep may be improved, and thereby an objective of lulling the child to sleep without adults may be achieved and an ability of the child to sleep on his or her own may be improved.

Different users may have different personal preferences. For example, in a family having more than one child, preference differences may exist among the more than one child due to different personalities, sexes, ages or the like. Thus, the video contents to be played that are determined by the display control method probably does not keep an attention of each of the more than one child in an optimum state, and therefore a child who needs to sleep early actually may not be lulled to sleep efficiently.

To solve the problem, optionally, the display control method is implemented only for a certain user. For example, when a family has more than one child and one of the more than one child is a baby, the certain user may be the baby when the baby needs to be lulled to sleep. In such a case, the display control method as shown in FIG. 1 may include step S104 before the step S102.

S104: recognizing identity.

Specifically, in the step S101, the identity information of all users within a range in which a camera may work may be collected by the camera. In such a case, the identity information of each of the user may be compared with preset identity information.

In case that the identity information of one of the users is matched with the preset identity information successfully, the step S102 is executed.

It should be noted that, the preset identity information is the identity information of the certain user. Specifically, the identity information may be facial and physical features of the certain user, or the age estimated based on the facial and physical features. In such a case, the facial and physical features or the age of the certain user may be inputted to form the preset identity information when the display control method is executed initially.

In such a way, the matching degree between the contents to be played determined through the display control method and the preference of the certain user is optimal, and thereby the attention of the certain user when watching or listening to the contents to be played may be improved and an optimal hypnotic effect may be achieved when lulling. Moreover, since attention of other children to the contents to be played is relatively low, influence on activities of other children may be reduced. In such a case, in case that the certain user is a baby which may be in a state of being lulled to sleep, influence of the contents to be played on brothers or sisters of the baby may be relatively low, so that they may still concentrate on their own activities.

Based on this, in order to further improve the match degree between the contents to be played and the preference of the user, the method as shown in FIG. 1 may further include step S105 to step S108.

S105: playing contents to be played.

Specifically, the contents to be played may include the first contents to be played with an effect of lulling a child to sleep and the second contents to be played with no effect of lulling a child to sleep.

S106: acquiring expression features.

Specifically, the expression features of the user may be acquired by the camera. The expression features may include gladness, fidgetiness, drowsiness, and etc.

S107: generating video preference data.

Specifically, the video preference data may be generated according to the expression features of the user.

For example, contents having been played may be added with a first tag in case that the user appears to be glad when watching or listening to the contents, and the first tag represents that the user may be interested in the contents having been played. Contents having been displayed may be added with a second tag in case that the user becomes drowsy when watching or listening to the contents, and the second tag represents the user is liable to fall asleep when watching or listening to the contents having been displayed. Contents having been displayed may be added with a third tag in case that the user appears to be fidgety when watching or listening to the contents, and the third tag represents the user may not be interested in the contents. The first tag, second tag and third tag may be included in the video preference data.

S108: optimizing data.

Specifically, video contents in the video database 10 may be adjusted according to the video preference data to optimize data. For example, video contents with the second tag may be taken as the contents to be played when it is determined in the step S103 that the current time is night. Video contents with the first tag may be taken as the contents to be played when it's determined in the step S103 that the current time is morning. Moreover, video contents with the third tag may be deleted automatically after being kept for a period of time or be putted into a recycle bin automatically and wait for the user to delete them.

Thus, the video contents in the video database 10 may be adjusted though the step S108 to save data processing time and power consumption when matching or invoking data. Moreover, since the video contents which the user are not interested in may be identified automatically, the user may delete the video contents to save storage space for data.

Figure 2:
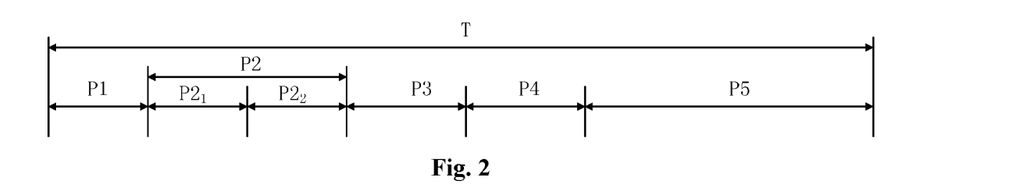
FIG. 2 is a schematic diagram of sleep stages in a sleep process in the embodiments of the present disclosure.

Based on this, when the display control method is used to lull a child or a baby to sleep, a sleep process of the child or the baby may be refined to differentiate different stages in the sleep process. For example, the sleep process T as shown in FIG. 2 may include a waking stage P1, a sleepy stage P2, a pre-sleep stage P3, a shallow sleep stage P4, and a deep sleep stage P5 and so on. Thus, lulling a child to sleep may be conducted stage by stage to achieve a better effect.

Figure 3:
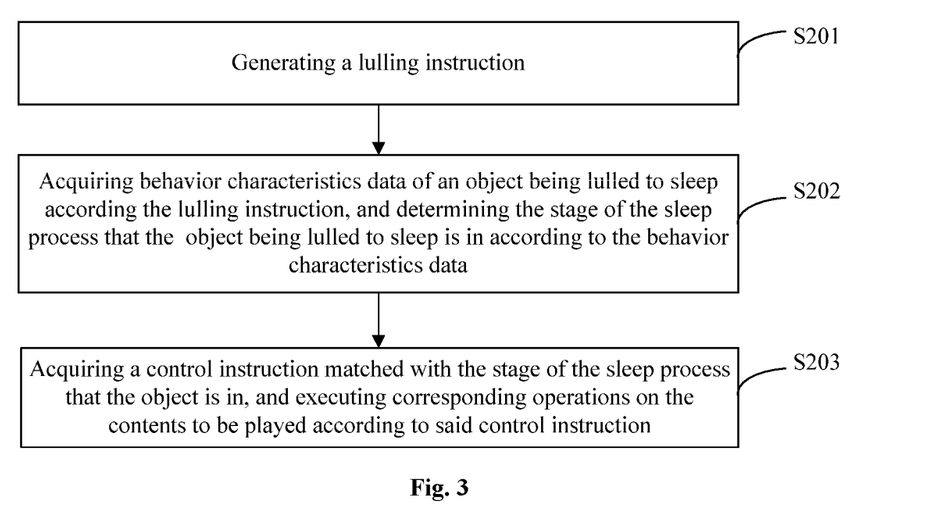
FIG. 3 is a flowchart of lulling a child to sleep by using the display control method shown in FIG. 1.

In order to achieve the objective, as shown in FIG. 3, the display control method may further include step S201 to step S203.

S201: generating a lulling instruction.

Figure 4:
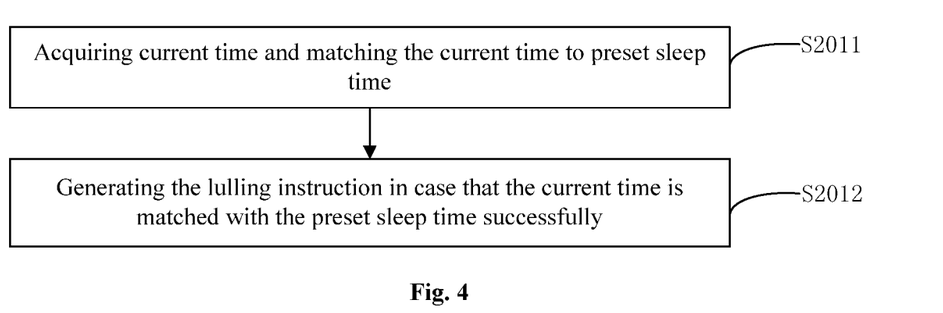
FIG. 4 is a detailed flowchart of a step of generating lulling instructions in the method provided in FIG. 3.

The lulling instruction may be sent from a guardian of a baby via voice or buttons in a remote control, or may be generated according to the acquired current time. Specifically, as shown in FIG. 4, the step S201 of generating a lulling instruction may include step 2011 to step 2012.

S2011: acquiring current time and matching the current time to preset sleep time.

The preset sleep time may be set by the guardian of the baby via voice or the button in the remote control, or may be a preset time that is built in default settings of a product. A fashion of setting the preset sleep time is not limited in the present disclosure. Based on this, after setting the preset sleep time, the display control method may further include recording a time length of the sleep process of the baby and adjusting the preset sleep time according to a result of the recording, to make the preset sleep time closer to an actual sleep time of the baby, so as to develop the sleep regularity of the baby.

S2012: generating the lulling instruction in case that the current time is matched with the preset sleep time successfully.

Step S202 may be executed after generating the lulling instruction.

S202: acquiring behavior characteristics data of an object being lulled to sleep according the lulling instruction, and determining the stage of the sleep process that the object being lulled to sleep is in according to the behavior characteristics data.

It should be noted that, the baby is taken as an example of the object being lulled to sleep, and the behavior characteristics date of the baby may include crying, mischief, rolling, blinking, rubbing eyes, kicking, smiling, laughing, babbling and the like.

Step S203 may be executed after determining the stage of the sleep process that the object being lulled to sleep is in.

S203: acquiring a control instruction matched with the stage of the sleep process that the object being lulled to sleep is in, and executing corresponding operations on the contents to be played according to said control instruction.

The baby is taken as the example of the object being lulled to sleep, and a detailed description of the step S203 is given with respect to different stages in the sleep process.

Specifically, in case that the behavior characteristics data of the baby acquired by the camera includes laughing, kicking, babbling and the like, it may be determined that the baby is in the waking stage P1 of the sleep process T. In such a case, the step S203 may include: acquiring a first control sub-instruction matched with the waking stage P1, selecting first video sub-contents matched with the waking stage P1 from contents to be played according the first control sub-instruction, and playing audio information and video information in the first video sub-contents.

It should be noted that, because the waking stage P1 belongs to the sleep process T, the baby in the waking stage P1 needs to shift to the deep sleep stage gradually. Thus, the first video sub-contents, as compared with the second contents to be played shown in FIG. 1 that are played when it is needless to lull the baby to sleep, should avoid the baby to become more excited after watching them.

Based on this and in order to further refine the sleepy stage of the sleep process T, optionally, the sleepy stage P2 may include a first sleepy stage $P2_1$ and a second sleepy stage $P2_2$, and the second sleepy stage $P2_2$ is closer to the pre-sleep stage P3 than the first sleepy stage $P2_1$.

Based on this, in case that the behavior characteristics data of the baby acquired by the camera includes crying or fidget, it may be determined that the baby is in the first sleepy stage $P2_1$ of the sleep process T1. In such a case, the step S203 may include: acquiring a second control sub-instruction matched with the first sleepy stage $P2_1$, and selecting second video sub-contents matched with the first sleepy stage $P2_1$ from the contents to be played according the second control sub-instruction, and playing audio information and video information in the second video sub-contents.

It should be noted that, in case that the baby changes his or her state from an excited state to the crying or fidget state and then gradually rubs his or her eyes, blinks and rolls after watching the first video sub-contents, it may be known that the first video sub-contents may make the baby to transit into the sleepy stage P2. Therefore, the second video sub-contents may be the same as the first video sub-contents. In case that the baby doesn't rub his or her eyes, blink or roll, then the second video sub-contents that have a better effect on pacifying the baby should be selected to replace the first video sub-contents.

Moreover, in case that the camera captures that the baby keeps rubbing eyes, blinking and rolling, it may be determined that the baby is in the second sleepy stage $P2_2$ of the sleep process T. The baby's keeping rubbing eyes, blinking and rolling may be a result achieved after watching the second video sub-contents, or may be a state that the baby gets into one his or her own without watching the second video sub-contents. A fashion in which the baby gets into the second sleepy stage $P2_2$ is not limited in the present disclosure. In such a case, the step S203 may include: acquiring a third control sub-instruction matched with the second sleepy stage $P2_2$, shutting down display of the video information of the contents to be played according to the third control sub-instruction, and outputting the audio information in the contents to be played. In case that the baby's being quiet is achieved after watching the second video sub-contents, videos in the second video sub-contents may be shut down and only audios in the second video sub-contents are played after the baby enters the second sleepy stage $P2_2$.

It should be noted that, in case that the baby does not rub eyes, blink or roll and cries again after the videos in the second video sub-contents are shut down, it may be determined that the baby may return to the first sleepy stage $P2_1$ of the sleep process T. In such case, the audio information and the video information in the second video sub-contents may be played simultaneously according to the second control sub-instruction matched with the first sleepy stage $P2_1$, to pacify the baby again.

Based on this, in case that the camera captures that eyes of the baby are closed, it may be determined that the baby is in the pre-sleep stage P3 of the sleep process T. In such a case, the step S203 may include: acquiring a fourth control sub-instruction matched with the third pre-sleep stage P3, shutting down display of the video information of the contents to be played according to the fourth control sub-instruction, and reducing an outputted volume of the audio information of the contents to be played. When the contents to be played are the second video sub-contents, the videos in the second video sub-contents may be shut down and the volume of the audios in the second video sub-contents may be reduced.

Moreover, in case that the camera captures that the baby is in a quiet state and in an immobile sleeping posture, and the state and the posture may be kept for a certain period of time, it may be determined that the baby is in the shallow sleep stage P4 of the sleep process T. In such a case, the step S203 may include: acquiring a fifth control sub-instruction matched with the shallow sleep stage P4, shutting down display of the video information in the contents to be played according to the fifth control sub-instruction, shutting down output of the audio information in the contents to be played. In case that the contents to be played are the second video sub-contents, videos in the second video sub-contents may be shutting down and the output of audios in the second video sub-contents may be turned off.

Finally, in case that the baby has no abnormal behavior within one hour after the baby entering the shallow sleep stage P4, it may be determined that the baby is in the deep sleep stage P5 of the sleep process T. In such a case, the step S203 may include: receiving a shutdown command, executing a shutdown operation, and turning off components of the display control device.

It should be noted that, during lulling a baby to sleep by using the display control method, when the display control device is started in accordance with the preset sleep time and the camera captures images initially, the display control device may collect the behavior characteristics data of the baby continually if the display control device collects that the baby is in the waking stage P1 of the sleep process T, and the display control device may lull the baby to sleep from the waking stage P1 and sequentially through the sleepy stage P2, the pre-sleep stage P3, the shallow sleep stage P4 and the deep sleep stage P5 in accordance with the method mentioned above, to cause the baby to get into the sleep stage finally.

Moreover, when the display control device is started in accordance with the preset sleep time and the camera captures images initially, if the display control device collects that the baby is in a stage other than the waking stage, for example the sleepy stage P2, of the sleep process T, then the display control device lulls the baby to sleep directly from the sleepy stage P2 and sequentially through the pre-sleep stage P3, the shallow sleep stage P4 and the deep sleep stage P5 in accordance with the method mentioned above, without lulling the baby to sleep from the waking stage P1 first and then through the sleepy stage P2.

Figure 5:
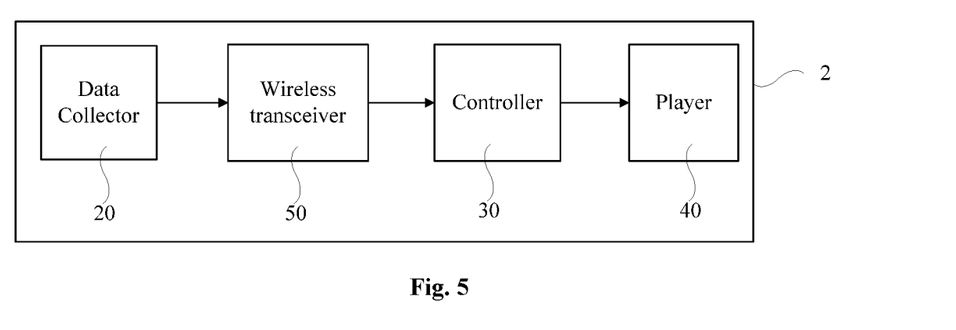
FIG. 5 is a structural schematic diagram of a display control device provided by the embodiments of the present disclosure.

The embodiments of the present disclosure provide a display control device 2, as shown in FIG. 5. The display control device 2 may include a data collector 20, a controller 30 and a player 40.

The data collector 20 is connected with the controller 30. The data collector 20 may collect current data, such as the current data of an object being lulled to sleep (such as a baby), and output a result of the collecting to the controller 30. The current data may include identity information of the object and current time.

It should be noted that, the data collector 20 may include a camera, for example a CCD (Charge Coupled Device) camera or a CMOS (Complementary Metal Oxide Semiconductor) camera.

The controller 30 may be also connected to the player 40. The controller 30 may be used to match the current data with feature parameters of video contents in a video database, and take the video contents as the contents to be played in case that the current data is matched with the feature parameters of the video contents successfully. The video contents may include the audio information and the video information.

Moreover, the player 40 may be used to play the contents to be played. The player 40 may include a display, such as a LCD (Liquid Crystal Display) or an OLED (Organic Light Emitting Diode) display. Moreover, the display may be a smart phone, a PDA, a projector or a television set, and a specific type of the display is not limited in the present disclosure.

The display control method for conducting a display control by using the display control device 2 is described above and will not be further described here.

Based on this, optionally, the display control device may further include a wireless transceiver 50. The data collector 20 may be connected with the controller 30 via the wireless transceiver 50 configured to transmit output signals of the data collector 20 to the controller 30 wirelessly. Thus, it may be prevented that the installation positions of the data collector 20 and the controller 30 are limited by cables.

Figure 6:
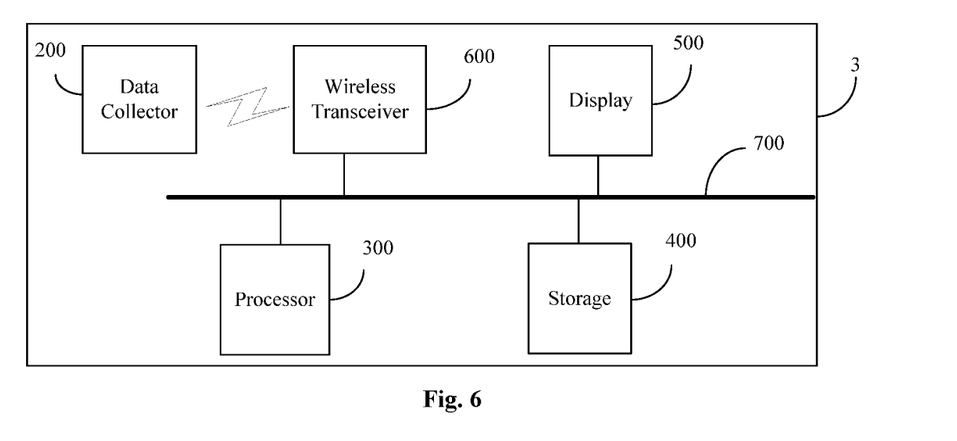
FIG. 6 is a structural schematic diagram of a display control device provided by the embodiments of the present disclosure.

The embodiments of the present disclosure further provide a display control device 3. As shown in FIG. 6, the display control device 3 may include a data collector 200, a processor 300, a storage 400, a display 500 and a wireless transceiver 600.

The data collector 200 may be connected with the processor 300, and may be configured to acquire a collecting result including the current data of an object (such as the current data of a baby considered as the object to be lulled to sleep) and output the collecting result to the processor 300. The current data may include identity information of the object and current time. The data collector 200 may include a camera, such as a CCD camera or a CMOS camera.

The storage 400 may be connected with the processor 300 via a bus 700 and be used to store video data.

The processor 300 may be configured to receive the collecting result including the current data of the object from the data collector 200, match the current data with the feature parameters of the video contents in the video database stored in the storage 400, and take the video contents as the contents to be played on the display 500 if the current data is matched with the feature parameters of the video contents successfully. The video contents may include audio information and video information.

The display 500 may be connected with the processor 300 via the bus 700 and be used to play the contents to be played under control of the processor 300. The display 500 may be a LCD display or an OLED display.

The wireless transceiver 600 may be connected with the processor 300 via the bus 700, and the data collector 200 may be connected with the wireless transceiver 600 wirelessly. The wireless transceiver 600 may be configured to receive the collecting result including the current data of the user collected by the data collector 200, and transmit the collecting result to the processor 300.

The embodiments of the present disclosure further provide a non-transient and non-volatile storage medium. Instructions and a video database may be stored on the non-transient and non-volatile storage medium, and when the instructions are executed by a processor, the following steps S1 to S3 may be executed by the processor.

S1: acquiring current data of a user, wherein the current data may include identity information of the user and current time.

Specifically, an interface may be presented by the processor to receive age and current time input by a user.

S2: matching the current data with feature parameters of video contents in the video database.

The matching between the current data of the user and the feature parameters of the video contents in the video database may include matching between the identity information of the user and the feature parameters of the video contents in the video database, i.e. matching identity, and matching between the current time with the feature parameters of the video contents in the video database, i.e. time determination. The video contents may include audio information and video information.

S3: setting the video contents as the contents to be played if the current data is matched with the feature parameters of the video contents successfully.

In summary, the current data may be collected through the display control device. On one hand, since the current data include the identity information of the user, the displayed contents may be in accord with the user's identity when the feature parameters of the contents to be played are matched successfully with the identity information of the user. Thus, a matching degree between the contents to be played and the user's interest and attention may be increased, so that the user, such as a child or a baby, may be in a state of concentrating in watching and listen when playing the contents to be played. On the other hand, since the current data may also include the current time, the contents to be played with feature parameters matched with the current time may be effective to lull the user to sleep if the current time is night. Thus, a child or a baby who has sufficient concentration may be hypnotized efficiently, an effect of lulling the child or the baby to sleep may be improved, and thereby the objective of lulling the child or the baby to sleep without adults may be achieved and the ability of the child or the baby to fall sleep on his or her own may be improved.

Those of ordinary skills in the art may understand that all or a part of the steps in the above embodiments of the method may be implemented through a program instructions and relevant hardware. The program instructions may be stored in a computer readable storage medium. When the program instructions are executed, the steps in the foregoing embodiments of the method are executed. The foregoing storage medium includes any medium that may store program codes, such as an ROM, an RAM, a magnetic disc, or a compact disc.

The above descriptions only illustrate specific ones of the embodiments of the present disclosure, and the protection scope of the present disclosure is not limited thereto. Variations or substitutions easily occurred to those skilled in the art within the teachings disclosed herein should fall into the protection scope of the present disclosure. Thus, the protection scope of the present disclosure is determined by the claims.

What is claimed is:

1. A display control method, comprising:
   acquiring current data of a user, the current data comprising identity information of the user and current time;
   determining contents to be played according to the current data and feature parameters of video contents in a video database, wherein the video contents comprise audio information and video information;
   generating a lulling instruction;
   acquiring behavior feature data of the user according to the lulling instruction, and determining a current stage of a sleep process that the user is in according to the behavior feature data; wherein the sleep process comprises a waking stage, a first sleepy stage, a second sleepy stage, a pre-sleep stage, a shallow sleep stage, and a deep sleep stage arranged sequentially; and
   acquiring control instructions matched with the current stage and subsequent stages of the current stage of the sleep process that the user is in respectively, and executing corresponding operations on the contents to be played according to the control instructions.

2. The display control method according to claim 1, further comprising:
   playing the contents to be played;
   acquiring expression features of the user, and generating video preference data according to the expression features; and
   adjusting the video contents in the video database according to the video preference data.

3. The display control method according to claim 1, wherein the generating a lulling instruction comprises:

acquiring the current time; and
generating the lulling instruction according to the current time and preset sleep time.

4. The display control method according to claim 3, further comprising:
recording a time length of the sleep process; and
adjusting the preset sleep time according to the recorded time length.

5. The display control method according to claim 1, wherein determining the current stage of the sleep process that the user is in according to the behavior feature data is the waking stage, the acquiring the control instructions matched with the current stage and subsequent stages of the current stage of the sleep process that the user is in respectively, and executing the corresponding operations on the contents to be played according to the control instructions, comprises:
acquiring a first control sub-instruction matched with the waking stage;
selecting first video sub-contents matched with the waking stage from the contents to be played according to the first control sub-instruction;
playing audio information and video information in the first video sub-contents;
acquiring a second control sub-instruction matched with the first sleepy stage;
selecting second video sub-contents matched with the first sleepy stage from the contents to be played according to the second control sub-instruction;
playing audio information and video information in the second video sub-contents;
acquiring a third control sub-instruction matched with the second sleepy stage;
shutting down display of the video information in the second video sub-contents according to the third control sub-instruction, and outputting the audio information in the second video sub-contents;
wherein the second sleepy stage is closer to the pre-sleep stage than the first sleepy stage;
acquiring a fourth control sub-instruction matched with the pre-sleep stage,
shutting down display of the video information in the second video sub-contents according to the fourth control sub-instruction, and reducing an outputted volume of the audio information in the second video sub-contents;
acquiring a fifth control sub-instruction matched with the shallow sleep stage;
shutting down display of the video information in the second video sub-contents according to the fifth control sub-instruction, and turning off output of the audio information in the second video sub-contents; and
receiving a shutdown instruction, and executing a shutdown operation in the deep sleep stage.

6. The display control method according to claim 1, wherein determining the current stage of the sleep process that the user is in according to the behavior feature data is the first sleepy stage, the acquiring the control instructions matched with the current stage and subsequent stages of the current stage of the sleep process that the user is in respectively, and executing the corresponding operations on the contents to be played according to the control instructions, comprises:
acquiring a first control sub-instruction matched with the first sleepy stage;
selecting video sub-contents matched with the first sleepy stage from the contents to be played according to the first control sub-instruction; and
playing audio information and video information in the video sub-contents;
acquiring a second control sub-instruction matched with the second sleepy stage;
shutting down display of the video information in the video sub-contents according to the second control sub-instruction, and outputting the audio information in the video sub-contents;
wherein the second sleepy stage is closer to a pre-sleep stage than the first sleepy stage;
acquiring a third control sub-instruction matched with the pre-sleep stage,
shutting down display of the video information in the video sub-contents according to the third control sub-instruction, and reducing an outputted volume of the audio information in the video sub-contents;
acquiring a fourth control sub-instruction matched with the shallow sleep stage;
shutting down display of the video information in the video sub-contents according to the fourth control sub-instruction, and turning off output of the audio information in the video sub-contents; and
receiving a shutdown instruction, and executing a shutdown operation in the deep sleep stage.

7. The display control method according to claim 1, wherein determining the current stage of the sleep process that the user is in according to the behavior feature data is the second sleepy stage, the acquiring the control instructions matched with the current stage and subsequent stages of the current stage of the sleep process that the user is in respectively, and executing the corresponding operations on the contents to be played according to the control instructions, comprises:
acquiring a first control sub-instruction matched with the second sleepy stage;
shutting down display of video information in the contents to be played according to the first control sub-instruction, and outputting audio information in the contents to be played;
wherein the second sleepy stage is closer to a pre-sleep stage than the first sleepy stage;
acquiring a second control sub-instruction matched with the pre-sleep stage, and
shutting down display of the video information in the contents to be played according to the second control sub-instruction, and reducing an outputted volume of the audio information in the contents to be played;
acquiring a third control sub-instruction matched with the shallow sleep stage;
shutting down display of the video information in the contents to be played according to the third control sub-instruction, and turning off output of the audio information in the contents to be played; and
receiving a shutdown instruction, and executing a shutdown operation in the deep sleep stage.

8. The display control method according to claim 1, wherein determining the current stage of the sleep process that the user is in according to the behavior feature data is the pre-sleep stage, the acquiring the control instructions matched with the current stage and subsequent stages of the current stage of the sleep process that the user is in respectively, and executing the corresponding operations on the contents to be played according to the control instructions, comprises:

acquiring a first control sub-instruction matched with the pre-sleep stage, and
shutting down display of video information in the contents to be played according to the first control sub-instruction, and reducing an outputted volume of audio information in the contents to be played;
acquiring a second control sub-instruction matched with the shallow sleep stage;
shutting down display of the video information in the contents to be played according to the second control sub-instruction, and turning off output of the audio information in the contents to be played; and
receiving a shutdown instruction, and executing a shutdown operation in the deep sleep stage.

9. The display control method according to claim 1, wherein determining the current stage of the sleep process that the user is in according to the behavior feature data is the shallow sleep stage, the acquiring the control instructions matched with the current stage and subsequent stages of the current stage of the sleep process that the user is in respectively, and executing the corresponding operations on the contents to be played according to the control instructions, comprises:
acquiring a control sub-instruction matched with the shallow sleep stage;
shutting down display of video information in the contents to be played according to the control sub-instruction, and turning off output of audio information in the contents to be played.

10. The display control method according to claim 1, wherein determining the current stage of the sleep process that the user is in according to the behavior feature data is the deep sleep stage, the acquiring the control instructions matched with the current stage and subsequent stages of the current stage of the sleep process that the user is in respectively, and executing the corresponding operations on the contents to be played according to the control instructions, comprises:
receiving a shutdown instruction, and executing a shutdown operation.

11. A non-transient storage medium, comprising instructions and a video database stored on the non-transient storage medium, wherein, when the instructions are executed by a processor, the processor executes the method according to claim 1.

12. A display control device, comprising:
a processor;
a data collector connected with the processor and configured to acquire current data of a user and output the current data to the processor, the current data comprising identity information of the user and current time; and
a storage connected with the processor and configured to store a video database,
wherein the processor is configured to:
acquire the current data of the user from the data collector,
determine contents to be played according to the current data and feature parameters of video contents in the video database,
wherein the video contents comprise audio information and video information;
generate a lulling instruction;
acquire behavior feature data of the user according to the lulling instruction, and determine a current stage of a sleep process that the user is in according to the behavior feature data; wherein the sleep process comprises a waking stage, a first sleepy stage, a second sleepy stage, a pre-sleep stage, a shallow sleep stage, and a deep sleep stage arranged sequentially; and
acquire control instructions matched with the current stage and subsequent stages of the current stage of the sleep process that the user is in respectively, and execute corresponding operations on the contents to be played according to the control instructions.

13. The display control device according to claim 12, further comprising:
a display, connected with the processor and configured to play the contents to be played; and
a wireless transceiver connected with the processor, wherein the data collector is connected with the processor through the wireless transceiver, and the wireless transceiver is configured to transmit output signals of the data collector to the processor wirelessly.

14. The display control device according to claim 12, wherein the processor is further configured to:
play the contents to be played;
acquire expression features of the user, and generate video preference data according to the expression features; and
adjust the video contents in the video database according to the video preference data.

15. The display control device according to claim 12, wherein the processor is further configured to:
acquire the current time, and
generate the lulling instruction according to the current time and preset sleep time.

* * * * *